United States Patent
Zinobile et al.

(10) Patent No.: US 8,318,977 B2
(45) Date of Patent: Nov. 27, 2012

(54) METHANOL CARBONYLATION SYSTEM HAVING ABSORBER WITH MULTIPLE SOLVENT OPTIONS

(75) Inventors: Raymond J. Zinobile, Houston, TX (US); Tommy W. Doggett, League City, TX (US); Lun-kuang Liu, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 306 days.

(21) Appl. No.: 12/386,808

(22) Filed: Apr. 23, 2009

(65) Prior Publication Data

US 2009/0270651 A1      Oct. 29, 2009

Related U.S. Application Data

(60) Provisional application No. 61/125,791, filed on Apr. 29, 2008.

(51) Int. Cl.
*C07C 51/12*   (2006.01)
*C07C 51/42*   (2006.01)

(52) U.S. Cl. .......... 562/519; 562/608

(58) Field of Classification Search .......... None
See application file for complete search history.

(56) References Cited

U.S. PATENT DOCUMENTS

| | | | |
|---|---|---|---|
| 2,938,017 A | 5/1960 | Grosser | 260/88.3 |
| 4,241,219 A * | 12/1980 | Wan | 560/232 |
| 5,001,259 A | 3/1991 | Smith et al. | 562/519 |
| 5,026,908 A | 6/1991 | Smith et al. | 562/519 |
| 5,144,068 A | 9/1992 | Smith et al. | 562/519 |
| 5,281,359 A | 1/1994 | Scates et al. | 252/182.16 |
| 5,334,755 A | 8/1994 | Yoneda et al. | 562/519 |
| 5,416,237 A * | 5/1995 | Aubigne et al. | 562/519 |
| 5,466,874 A | 11/1995 | Scates et al. | 562/519 |
| 5,502,243 A | 3/1996 | Waller et al. | 560/232 |
| 5,696,284 A | 12/1997 | Baker et al. | 560/232 |
| 5,770,768 A | 6/1998 | Denis et al. | 562/519 |
| 5,877,347 A | 3/1999 | Ditzel et al. | 562/519 |
| 5,877,348 A | 3/1999 | Ditzel et al. | 562/519 |
| 5,883,295 A | 3/1999 | Sunley et al. | 562/519 |
| 5,932,764 A | 8/1999 | Morris et al. | 562/519 |

(Continued)

FOREIGN PATENT DOCUMENTS

CN    ZL92108244.4    6/1999

(Continued)

OTHER PUBLICATIONS

See attached Database Caplus Chemical Abstracts Service, Columbus, Ohio, US; Database Accession No. Abstract No. 2006:284105, Chen et al., JP 1651388 "Process for preparation of acetic acid and acetic anhydride".*

(Continued)

*Primary Examiner* — Karl J Puttlitz
(74) *Attorney, Agent, or Firm* — Michael W. Ferrell

(57) ABSTRACT

A methanol carbonylation system 10 includes an absorber tower 75 adapted for receiving a vent gas stream and removing methyl iodide therefrom with a scrubber solvent, the absorber tower being coupled to first and second scrubber solvent sources 16, 56 which are capable of supplying different first and second scrubber solvents. A switching system including valves 90, 92, 94, 96, 98 alternatively provides first or second scrubber solvents to the absorber tower and returns the used solvent and sorbed material to the carbonylation system to accommodate different operating modes.

27 Claims, 2 Drawing Sheets

U.S. PATENT DOCUMENTS

| | | | |
|---|---|---|---|
| 5,942,460 A | 8/1999 | Garland et al. | 502/150 |
| 6,657,078 B2 | 12/2003 | Scates et al. | 562/519 |
| 2008/0293967 A1 | 11/2008 | Scates et al. | 562/517 |

FOREIGN PATENT DOCUMENTS

| | | |
|---|---|---|
| CN | 200410016120 | 7/2007 |
| CN | 1651388 | * 11/2007 |
| DE | 2 059 484 | 6/1972 |
| EP | 0 013 804 | 8/1980 |
| EP | 0 567 331 A2 | 10/1993 |
| EP | 0 759 419 A1 | 2/1997 |
| GB | 2 112 394 A | 7/1983 |

OTHER PUBLICATIONS

English Translation of CN 1651388 (2005).*
Research Report from 2006 Forum of The Southwest Research & Design Institute of Chemical Industry (Slides 1-32), entitled "Process of 200ktpa Methanol Low Press Oxo Synthesis AA".

* cited by examiner

METHANOL CARBONYLATION SYSTEM HAVING ABSORBER WITH MULTIPLE SOLVENT OPTIONS

CLAIM FOR PRIORITY

This non-provisional application claims the benefit of the filing date of U.S. Provisional Patent Application Ser. No. 61/125,791, of the same title, filed Apr. 29, 2008. The priority of U.S. Provisional Patent Application Ser. No. 61/125,791 is hereby claimed and the disclosure thereof is incorporated into this application by reference.

TECHNICAL FIELD

The present invention relates to acetic acid production and, in particular, to a methanol carbonylation system with a light ends absorber adapted to use different scrubber solvents and return the used solvent to the carbonylation system.

BACKGROUND OF THE INVENTION

Acetic acid production by way of methanol carbonylation is known in the art. Generally speaking, a methanol carbonylation production line includes a reaction section, a purification section, light ends recovery and a catalyst reservoir system. In the reaction section, methanol and carbon monoxide are contacted with rhodium or iridium catalyst in a homogenous stirred liquid phase reaction medium in a reactor to produce acetic acid. Methanol is pumped to the reactor from a methanol surge tank. The process is highly efficient, having a conversion of methanol to acetic acid of typically greater than 99 percent. The reaction section also includes a flash vessel coupled to the reactor which flashes a draw stream in order to remove crude product from the reaction section. The crude product is fed to a purification section which includes generally a light ends or stripper column, a drying column, auxiliary purification and optionally a finishing column. In the process, various vent streams containing light ends, notably methyl iodide, carbon monoxide and methyl acetate are generated and fed to the light ends recovery section. These vent streams are scrubbed with a solvent to remove the light ends which are returned to the system or discarded.

In a traditional, Monsanto methanol carbonylation plant, a high pressure and low pressure absorber are included wherein acetic acid is used as the scrubber solvent. The acetic acid solvent must subsequently be stripped of light ends, usually in another purification column so that the acid is not wasted. Such columns are expensive because they must be made of a highly corrosion resistant material such as zirconium alloys and so forth. Moreover, stripping light ends from the acid requires steam and contributes to operating expense.

Nevertheless, using acetic acid as a scrubber solvent is widespread in the carbonylation art generally. See for example, U.S. Pat. No. 5,502,243 to Waller et al., entitled "Hydrocarbonylation of Dimethyl Ether". Note the disclosure at FIG. 3, and the discussion at Cols. 8 and 9 concerning operation of an absorber 321. A cool acetic stream 323 passes downwardly through this absorber and absorbs any residual co-products and volatile catalyst components from the vent gas.

So also, there is disclosed in U.S. Pat. No. 4,241,219 to Wan, entitled "Treatment of Carbonylation Effluent", a method of recovering volatile components by contact with a scrubbing solvent recovered from the reaction mixture in the same production line. See Col. 2, lines 15-30 wherein it is noted that acetic anhydride, ethylidene diacetate, acetic acid, or mixtures of them can be used as a vent gas scrubber solvent.

Methanol has been suggested for use as a scrubber solvent in connection with a methanol carbonylation process. In this regard, see U.S. Pat. No. 5,416,237 to Aubigne et al., entitled "Process for the Production of Acetic Acid". It is noted in the '237 patent that noncondensables from a flash tank vapor overhead may be scrubbed countercurrently with chilled methanol. The methanol scrubber solvent residual stream is added to pure methanol and then used as feed to the reactor. See Col. 9, lines 30-42. If the reactor is not consuming the residual stream, it must be stored separately or purified again contributing to capital expense and operating costs.

Chinese Patent Application Publication No. 200410016120.7 discloses a method for recovering light components in vent gas from production of acetic acid/acetic anhydride by way of scrubbing with methanol and acetic acid. The system disclosed in the Publication No. 200410016120.7 discloses a two stage absorption arrangement wherein vent gas is treated sequentially with two different absorbents in a two stage system. Note particularly FIG. 2. Another system is seen in an industrial publication entitled "Process of 200 ktpa Methanol Low Press Oxo Synthesis AA" (SWRDICI 2006) (China). In this research publication there is shown a vent gas treatment system including a high pressure absorber as well as a low pressure absorber. Both absorbers of this system are operated utilizing methanol as a scrub fluid.

While there have been advances in the art, known methods of scrubbing vent gases in methanol carbonylation systems typically involve multiple absorber towers which are expensive to fabricate and operate. In accordance with the invention, there is provided an improved methanol carbonylation system with an absorber capable of using different solvents. The inventive system reduces both capital requirements and operating costs as compared with conventional systems.

SUMMARY OF THE INVENTION

There is provided a carbonylation system for making acetic acid having an absorber tower with multiple scrubber solvent options for treating vent gas. The absorber recovers methyl iodide and other volatiles such as methyl acetate vapor from the vent gas with scrubber solvent, the tower being coupled to first and second scrubber solvent sources which are capable of supplying different scrubber solvents. Typically, methanol is used as a scrubber solvent in a steady state mode of operation, while acetic acid may be used during start-up or transient operation of the unit. A switching system alternatively provides either methanol or acetic acid to the tower and returns the solvent and recovered volatiles to the carbonylation system for further reaction. During changeover of scrubber solvents, the recovered material may be added to the catalyst reservoir system if so desired.

The use of a one column system light ends absorber in accordance with the invention allows operation without the need for a dedicated light ends stripper for recovering methyl iodide from the system offgas vent stream. A salient benefit is capital reduction for new acetic acid carbonylation projects (eliminate stripper column system, reboiler, subcooler, and associated instrumentation and piping) by being able to use one absorber system on two different scrub mediums to accommodate all modes of operation including: startup, normal operation, upset operation and shutdown. Another benefit is energy reduction for normal operation via steam savings realized by elimination of the need for an auxiliary stripper column for scrubber solvent. Still another benefit is better scrub of light ends component methyl iodide by using subchilled 5-15° C. methanol for a normal operation mode.

Further details and advantages will be apparent from the discussion which follows.

BRIEF DESCRIPTION OF THE DRAWINGS

The invention is described in detail below with reference to the appended drawings, wherein like numerals designate similar parts. In the drawings.

DETAILED DESCRIPTION OF THE INVENTION

Figure 1:
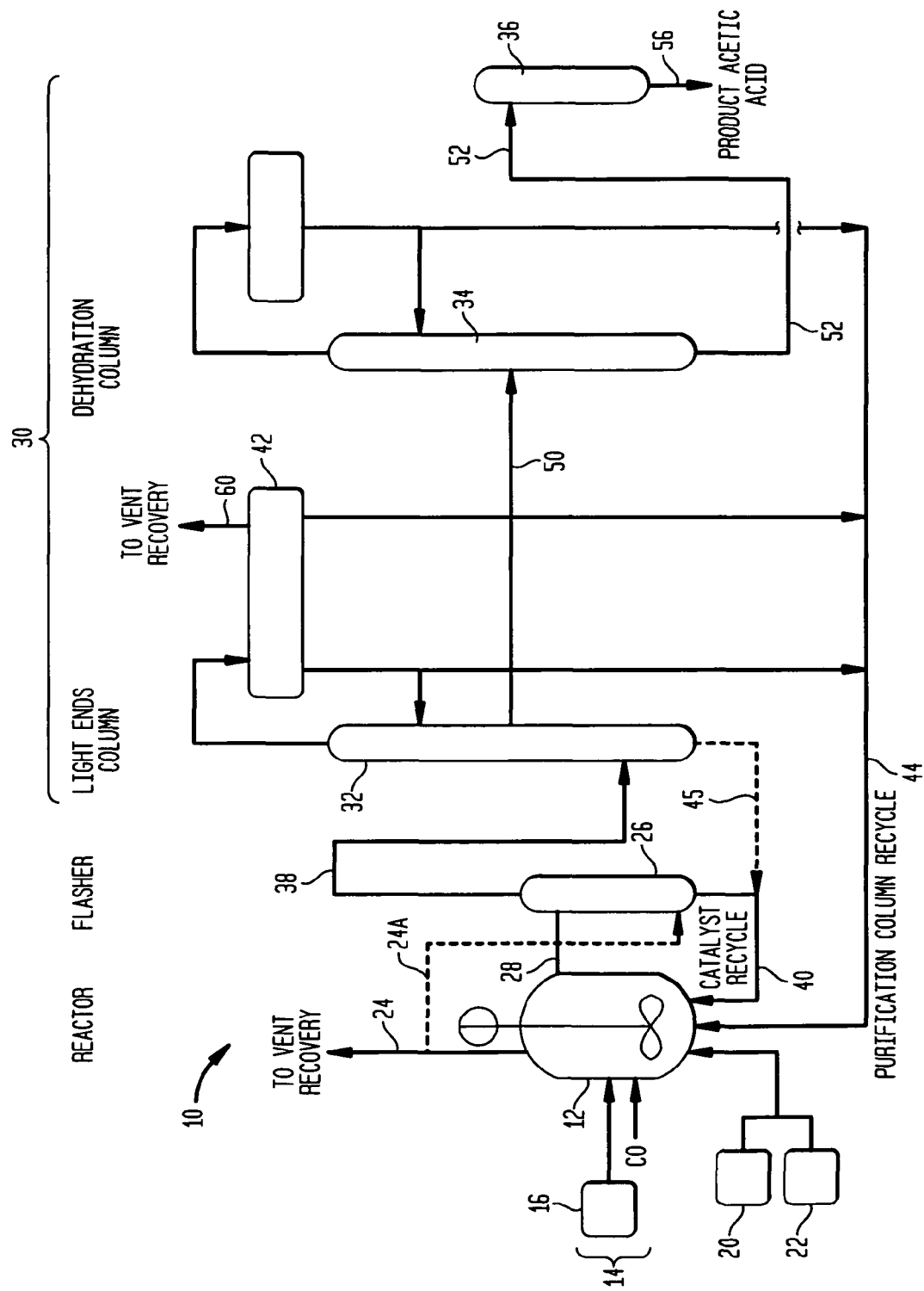
FIG. 1 is a schematic diagram illustrating a carbonylation system for making acetic acid and FIG. 2 is a schematic diagram illustrating a vent gas absorber and switching system used in connection with the system of FIG. 1.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. % and like terms refer to weight percent, unless otherwise indicated.

"Consisting essentially of" and like terminology refers to a composition consisting of 90% by weight or more of the specified component. Thus a scrubber solvent stream consists essentially of methanol if it is at least 90% methanol.

"Low pressure" and like terminology refers to pressures much lower than the pressure maintained in a carbonylation reactor of the class discussed herein. Low pressure thus refers to gauge pressures generally less than 10 bar, suitably less than 5 bar, typically less than about 3 bar and in some cases less than 1 bar.

"Volatile" components are those compounds in vapor phase and/or having a boiling point below or equal to that of methyl acetate including methyl iodide.

As used herein the "purified process stream" includes the process stream fed forward from the light ends column, and any subsequent purifications of the light ends process stream.

A Group VIII catalyst metal used in connection with the present invention may be a rhodium and/or iridium catalyst. The rhodium metal catalyst may be added in any suitable form such that rhodium is in the catalyst solution as an equilibrium mixture including $[Rh(CO)_2I_2]^-$ anion as is well known in the art. When rhodium solution is in the carbon monoxide-rich environment of the reactor, solubility of the rhodium is generally maintained because rhodium/carbonyl iodide anionic species are generally soluble in water and acetic acid. However, when transferred to carbon monoxide depleted environments as typically exist in the flasher, light ends column and so forth, the equilibrium rhodium/catalyst composition changes since less carbon monoxide is available. Rhodium precipitates as $RhI_3$, for example; details as to the form of entrained rhodium downstream of the reactor is not well understood. Iodide salts help alleviate precipitation in the flasher under so-called "low water" conditions as will be appreciated by one of skill in the art.

Iodide salts maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The iodide salt may be added as a mixture of salts such as a mixture of lithium iodide and sodium iodide and/or potassium iodide. Alternatively, the iodide salt may be generated in-situ since under the operating conditions of the reaction system, a wide range of non-iodide salt precursors such as alkali metal acetates will react with methyl iodide to generate the corresponding co-promoter iodide salt stabilizer. Suitable salts can be generated in situ from non-ionic precursors, such as a phosphine oxide or any suitable organic ligand or ligands if so desired. Phosphine oxides and suitable organic ligands generally undergo quaternization in the presence of methyl iodide at elevated temperatures to yield salts which maintain iodide anion concentration. For additional detail regarding iodide salt generation, see U.S. Pat. No. 5,001,259 to Smith et al.; U.S. Pat. No. 5,026,908 to Smith et al.; and U.S. Pat. No. 5,144,068, also to Smith et al., the disclosures of which are hereby incorporated by reference.

An iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

A supported Group VIII catalyst may employed if so desired. One preferred system includes an insoluble polymer having pendent pyrrolidone groups which support a rhodium species. One suitable catalyst is a poly-vinylpyrrolidone which has been crosslinked and rhodium loaded. Cross-linking can be achieved using a caustic catalyst as disclosed in U.S. Pat. No. 2,938,017 or by using a cross-linking agent such as disclosed in German 2,059,484. These references are herein incorporated by reference. This catalyst is prepared by reacting the polymer support with an alkyl halide and a rhodium compound. Both reactions are readily accomplished by standard procedures and using known components for such reactions. For example, it is preferred to simply add an amount of the insoluble polymer such as in powder or resin bead form to what otherwise constitutes as the homogeneous medium for the methanol carbonylation reaction. Such carbonylation reaction medium includes methanol and/or methyl acetate, acetic acid and a small amount of water in a pressure vessel along with a rhodium compound and an iodide promoter as described herein. Further details appear in U.S. Pat. No. 5,466,874, the disclosure of which is incorporated herein by reference in its entirety.

Another system includes an insoluble, pyridine ring-containing polymer, and a Group VIII metal supported thereon and is known per se. The term "pyridine ring-containing polymer" used herein is intended to refer to a polymer containing substituted or non-substituted pyridine rings or substituted or non-substituted, pyridine-containing polycondensed rings such as quinoline rings. The substituents include those inert to the methanol carbonylation such as an alkyl group and alkoxy group. Typical examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and di-vinylbenzene, copolymers of styrene, vinylbenzene and divinylbenzene, copolymers of vinylmethylpyridine and divinylbenzene and copolymers of vinylpyridine, methyl acrylate and ethyl diacrylate. Further details appear in U.S. Pat. No. 5,334, 755, the disclosure of which is incorporated herein by reference in its entirety.

Methyl iodide is used as the promoter. Preferably, the concentration of methyl in the liquid reaction composition is in the range 1 to 50% by weight, preferably 2 to 30% by weight.

The promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbonylation apparatus or process that is the subject of the invention typically includes a reactive section, purification section, a catalyst reservoir system and a light ends recovery system. The present invention may be appreciated in connection with, for example, the carbonylation of methanol with carbon monoxide in a homogeneous catalytic reaction system comprising a reaction solvent (typically acetic acid), methanol and/or its reactive derivatives, a soluble rhodium catalyst, at least a finite concentration of water. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range 0.1 to 16% by weight, more preferably 1 to 14% by weight, most preferably 1 to 10% by weight.

The reaction liquid is typically drawn from the reactor and flashed in a one step or multi-step process using a converter as well as a flash vessel as hereinafter described. The crude vapor process stream from the flasher is sent to a purification system which generally includes at least a light ends column and a dehydration column. As noted earlier, the form of any catalyst metal which is entrained to the light ends column and beyond is not well understood; however, the entrained catalyst metal is lost in conventional systems.

The present invention is further appreciated by reference to FIG. 1 which is a schematic diagram illustrating a typical carbonylation process and apparatus. In FIG. 1 there is shown a carbonylation system 10 including a reactor 12 provided with a feed system 14 including a methanol surge tank 16 and a carbon monoxide feed line. A catalyst reservoir system includes a methyl iodide storage vessel 20 as well as a catalyst storage tank 22. Reactor 12 is provided with a vent 24 and an optional vent 24a. Reactor 12 is coupled to a flash vessel 26 by way of a conduit 28 and optionally by way of vent 24a. The flasher, in turn, is coupled to a purification section 30 which includes a light ends or stripper column 32, a dehydration column 34 and a strong acid, silver-exchanged cation ion-exchange resin bed 36 which removes iodides from the product. Instead of a silver-exchanged, strong acid cation ion-exchange resin, it has been reported that anion ion-exchange resin can be used to remove iodides. See British Patent No. G 2112394A, as well as U.S. Pat. No. 5,416,237, Col. 7, lines 54+, which teaches the use of 4-vinylpyridine resins for iodide removal.

Figure 2:
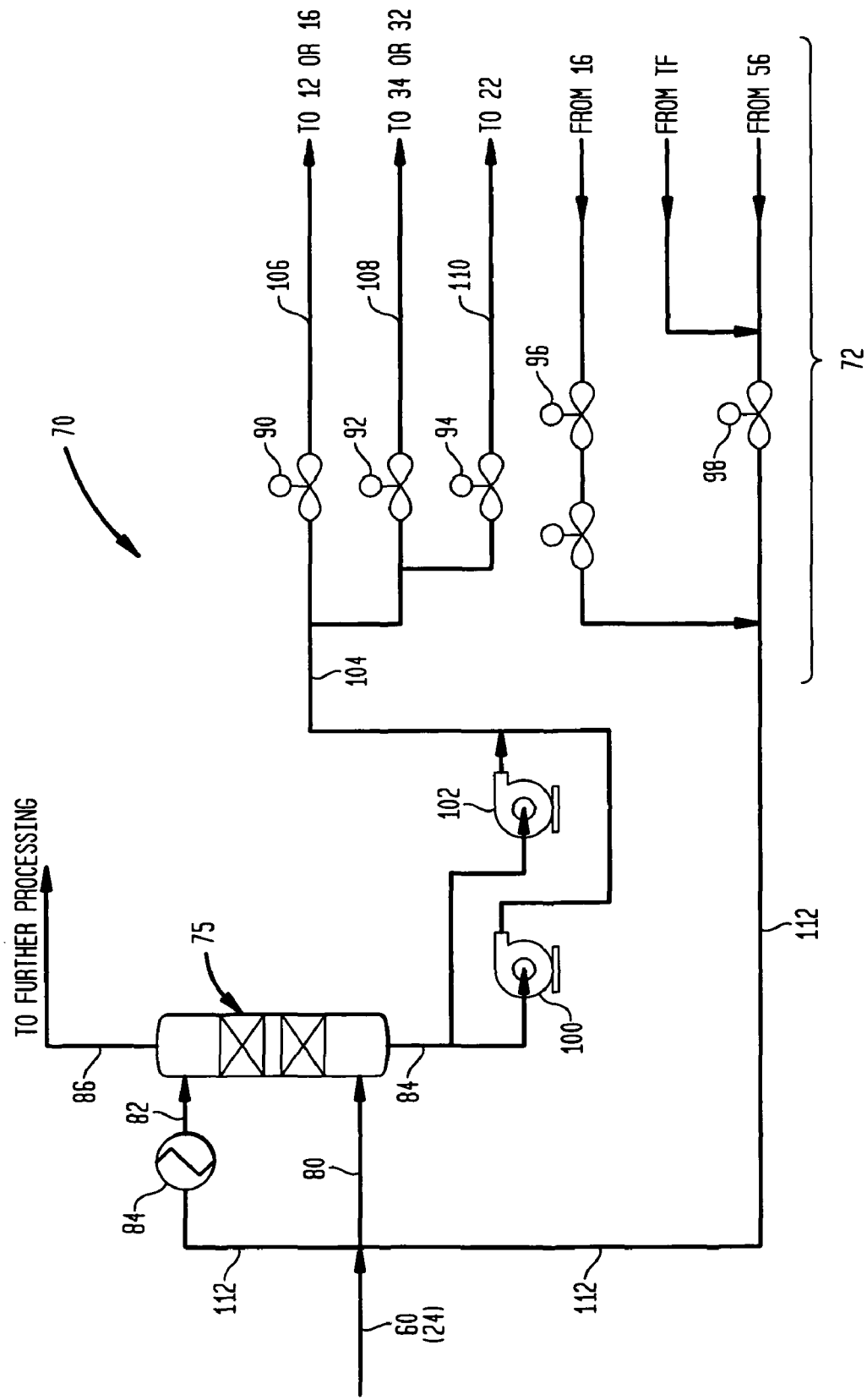

A gaseous purge stream is typically vented from the head of the reactor to prevent buildup of gaseous by-products such as methane, carbon dioxide and hydrogen and to maintain a set carbon monoxide partial pressure at a given total reactor pressure. A very significant improvement in processing involves minimizing or eliminating the high pressure vent from reactor 12 via line 24 to a high pressure absorber and instead utilizing a vent line such as line 24a. When operating at low water conditions as described herein, by-products and vent requirements are much reduced such that non-condensables can be vented at low pressure after flashing and stripping the light ends as is seen in FIGS. 1 and 2 while maintaining a predetermined carbon monoxide partial pressure in the reactor. Thus, the use of a high pressure absorber can be eliminated and/or minimized saving capital and operating costs.

Optionally (as illustrated in Chinese Patent No. ZL92108244.4), a so-called "converter" reactor can be employed which is located between the reactor and flasher vessel shown in FIG. 1. Optionally, the gaseous purge streams may be vented through the flasher base liquid or lower part of the light ends column to enhance rhodium stability and/or they may be combined with other gaseous process vents (such as the purification column overhead receiver vents) prior to scrubbing. Carbon monoxide may be added directly to a converter vessel if so desired or may be added slightly before (upstream) or after (downstream) if so desired in order to stabilize the catalyst solution and consume any unreacted methanol. Details of such arrangements are seen in European Patent No. EP 0 759 419 as well as U.S. Pat. No. 5,770,768 to Denis et al., the disclosures of which are hereby incorporated by reference.

These variations are well within the scope of the present invention as will be appreciated from the appended claims and the description which follows.

As will be appreciated by one of skill in the art, the different chemical environments encountered in the purification train may require different metallurgy. For example, equipment at the outlet of the light ends column will likely require a zirconium vessel due to the corrosive nature of the process stream, while a vessel of stainless steel may be sufficient for equipment placed downstream of the dehydration column where conditions are much less corrosive.

Carbon monoxide and methanol are introduced continuously into reactor 12 with adequate mixing at a high carbon monoxide partial pressure. The non-condensable bi-products are vented from the reactor to maintain an optimum carbon monoxide partial pressure. The reactor off gas is treated to recover reactor condensables, i.e., methyl iodide before flaring. Methanol and carbon monoxide efficiencies are generally greater than about 98 and 90% respectively. As will be appreciated from the Smith et al. patent noted above, major inefficiencies of the process are the concurrent manufacture of carbon dioxide and hydrogen by way of the water gas shift reaction.

From the reactor, a stream of the reaction mixture is continuously fed via conduit 28 to flasher 26. Through the flasher the product acetic acid and the majority of the light ends (methyl iodide, methyl acetate, water) are separated from the reactor catalyst solution, and the crude process stream 38 is forwarded with dissolved gases to the distillation or purification section 30 in single stage flash. The catalyst solution is recycled to the reactor via conduit 40.

The purification of the acetic acid typically includes distillation in a light ends column, a dehydration column, and, optionally, a heavy ends column. The crude vapor process stream 38 from the flasher is fed into the light ends column 32. Methyl iodide, methyl acetate, and a portion of the water condense overhead in the light end columns to form two phases (organic and aqueous) in a receiver 42. Both overhead liquid phases return to the reaction section via recycle line 44. Optionally, a liquid recycle stream 45 from the light ends column may also be returned to the reactor.

The purified process stream 50 is drawn off the side of the light ends column 32 and is fed into dehydration column 34. Water and some acetic acid from this column separate and are recycled to the reaction system via recycle line 44 as shown. The purified and dried process stream 52 from the dehydration column 34 feeds resin bed 36 and product is taken therefrom at 56 as shown. Carbonylation system 10 uses only two primary purification columns and is preferably operated as described in more detail in U.S. Pat. No. 6,657,078 to Scates et al., entitled "Low Energy Carbonylation Process", the disclosure of which is incorporated herein by reference. Additional columns are generally used as desired, depending on the system.

Receiver 42 is vented via line 60 to the light ends recovery system 70 shown in FIG. 2 which includes a switching system 72 which has a plurality of valves and pumps in order to selectively couple system 70 to scrubber solvent sources and return the used scrub solvent to the desired point in the carbonylation system as hereinafter described. Note also reactor 12 may be directly vented to system 70 via line 24 if necessary.

Light ends recovery system 70 has an absorber tower 75 which is fed with vent gas via line 80 and with scrubber solvent via line 82. Preferably the scrubber solvent is chilled with a chiller 84 prior to being fed to tower 75 wherein the solvent flows countercurrently with respect to the vent gas, absorbing methyl iodide and additional relative components before exiting the tower via return line 84 and being returned to the carbonylation unit. The scrubbed vent gas exits the tower at 86 and is further processed. For example, a second stage water scrub could be used to remove methyl acetate, methanol, acetic acid and so forth before flaring if so desired. Alternatively, a second stage water scrub could be provided in tower 75 if so desired. Preferably, more than 90% of the methyl iodide is removed from the vent gas. The scrubber fluid is generally chilled to a temperature of from about 5° C. to about 25° C. prior to use in the tower, with the proviso that when acetic acid is used as the scrubber solvent, the temperature of the solvent is held at 17° C. or more to prevent freezing.

Switching system 72 includes a plurality of valves such as valves 90, 92, 94, 96, 98 and one or more pumps 100, 102 to raise pressure in the return lines 104, 106, 108, 110 if needed. Feed valves 96, 98 are used to select the scrubber solvent which may be methanol from tank 16 or acetic acid from stream 56 depending upon the mode of operation of tower 75.

In steady state operation of carbonylation system 10 valve 98 is closed and methanol is fed from tank 16 through open valve 96 via line 112 to chiller 84, wherein the methanol is cooled. From the chiller, methanol is fed to tower 75, where it flows countercurrently with vent gas and sorbs methyl iodide and other volatile components therefrom before exiting the column via line 84. The used solvent with sorbed methyl iodide is pumped back to reactor 12 or tank 16 with pumps 100, 102 via line 106. In this mode of operation valves 92, 94 are closed and valve 90 is open.

During start up or shut down of the system it may be desirable to operate tower 75 using acetic acid as the scrub solvent. In this mode of operation, valve 98 is open and valve 96 is closed. Acid may be sourced from product stream 56 or a tank from (TF) if so desired. The acid flows through line 112 to chiller 84 where it is chilled and fed to tower 75 via line 82 and scrubs the vent gas supplied via lines 60, 80 as noted above. The acid exits the tower 75 via line 84 and is pumped back to the carbonylation system by way of pumps 100, 102 via lines 104, 108. In this mode of operation of tower 75, valves 90, 94 are closed and valve 92 is open so that the used acetic acid is returned to light ends column 32, the dehydration column 34, or elsewhere in the purification system for stripping.

During changeover from one solvent to the other, such as from methanol to acetic acid, it is generally undesirable to return the scrub fluid to the methanol feed system or light ends column since inefficiencies result. For such, a changeover may be accomplished in from about 5 to about 20 minutes, during which time the used scrubber solvent is fed to catalyst reservoir 22. In changeover mode, valves 90, 92 are closed and valve 94 is open. Thus the system is operated generally by way of (a) feeding vent gas from the carbonylation unit to the absorber tower, the vent gas including methyl iodide and optionally additional volatile components; (b) supplying a first scrubber solvent to the absorber tower, the first scrubber solvent consisting essentially of acetic acid; (c) contacting the vent gas with the first scrubber solvent thereby removing methyl iodide and optionally additional volatile components from the gas and absorbing methyl iodide and optionally additional volatile components into the first scrubber solvent; (d) feeding an absorber return stream including first scrubber solvent and absorbed methyl iodide and optionally additional absorbed volatile components to the light ends column, the dehydration column or elsewhere in the purification system; (e) terminating the supply of first scrubber solvent to the absorber tower; (f) supplying a second scrubber solvent to the absorber tower, the second scrubber solvent consisting essentially of methanol; (g) contacting the vent gas with the second scrubber solvent thereby removing methyl iodide and optionally additional volatile components from the gas and absorbing methyl iodide and optionally additional volatile components into the second scrubber solvent; (h) feeding an absorber return stream including first scrubber solvent, second scrubber solvent, absorbed methyl iodide and optionally additional absorbed volatile components from the absorber tower to the reactor; and (i) following the transition period, continue feeding an absorber return stream including second scrubber solvent and absorbed methyl iodide and optionally additional absorbed volatile components to the reactor. Feed to the absorber tower is selected by operation of valves 96, 98.

While the invention has been illustrated in connection with a particular apparatus, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A method of operating an absorber tower in a carbonylation unit for making acetic acid of the class including a reactor and a light ends column comprising:
   (a) feeding vent gas from the carbonylation unit to the absorber tower, the vent gas including methyl iodide and optionally additional volatile components;
   (b) supplying a first scrubber solvent to the absorber tower, the first scrubber solvent consisting essentially of acetic acid;
   (c) contacting the vent gas with the first scrubber solvent thereby removing methyl iodide and optionally additional volatile components from the gas and absorbing methyl iodide and optionally additional volatile components into the first scrubber solvent;
   (d) feeding an absorber return stream including first scrubber solvent and absorbed methyl iodide and optionally additional absorbed volatile components to the light ends column and/or dehydration column;
   (e) terminating the supply of first scrubber solvent to the absorber tower;
   (f) supplying a second scrubber solvent to the absorber tower, the second scrubber solvent comprising methanol, methyl acetate or mixtures thereof;
   (g) contacting the vent gas with the second scrubber solvent thereby removing methyl iodide and optionally additional volatile components from the gas and absorbing methyl iodide and optionally additional volatile components into the second scrubber solvent; and
   (h) feeding an absorber return stream including second scrubber solvent and absorbed methyl iodide and optionally additional absorbed volatile components to the reactor.

2. The method according to claim 1, wherein said second scrubber solvent consists essentially of methanol.

3. The method according to claim 1, further comprising the step of chilling the first scrubber solvent prior to supplying it to the absorber tower.

4. The method according to claim 1, further comprising the step of chilling the second scrubber solvent prior to supplying it to the absorber tower.

5. The method according to claim 1, further comprising mixing the second scrubber solvent and absorbed methyl iodide and optional additional absorbed volatile components with methanol or a reactive derivative thereof prior to feeding the used solvent to the reactor.

6. The method according to claim 1, wherein the vent gas includes methyl acetate and the first and second scrubber solvents are effective to absorb methyl acetate from the vent gas.

7. A method of operating an absorber tower in a carbonylation unit for making acetic acid of the class including a reactor and a light ends column comprising:
   (a) feeding vent gas from the carbonylation unit to the absorber tower, the vent gas including methyl iodide and optionally additional volatile components;
   (b) supplying a first scrubber solvent to the absorber tower, the first scrubber solvent consisting essentially of acetic acid;
   (c) contacting the vent gas with the first scrubber solvent thereby removing methyl iodide and optionally additional volatile components from the gas and absorbing methyl iodide and optionally additional volatile components into the first scrubber solvent;
   (d) feeding an absorber return stream including first scrubber solvent and absorbed methyl iodide and optionally additional absorbed volatile components to the light ends column and/or dehydration column;
   (e) terminating the supply of first scrubber solvent to the absorber tower;
   (f) supplying a second scrubber solvent to the absorber tower, the second scrubber solvent consisting essentially of methanol;
   (g) contacting the vent gas with the second scrubber solvent thereby removing methyl iodide and optionally additional volatile components from the gas and absorbing methyl iodide and optionally additional volatile components into the second scrubber solvent;
   (h) feeding an absorber return stream including first scrubber solvent, second scrubber solvent, absorbed methyl iodide and optionally additional absorbed volatile components from the absorber tower to the reactor during a transition period; and
   (i) following the transition period, continue feeding an absorber return stream including second scrubber solvent and absorbed methyl iodide and optionally additional absorbed volatile components to the reactor.

8. The method according to claim 7, wherein said second scrubber solvent consists of methanol.

9. The method according to claim 7, further comprising the step of chilling the first scrubber solvent prior to supplying it to the absorber tower.

10. The method according to claim 7, further comprising the step of chilling the second scrubber solvent prior to supplying it to the absorber tower.

11. The method according to claim 7, further comprising mixing the second scrubber solvent and absorbed methyl iodide and optional additional absorbed volatile components with methanol or a reactive derivative thereof prior to feeding the used solvent to the reactor.

12. A method of operating an absorber tower in a carbonylation unit for making acetic acid of the class including a reactor and a light ends column comprising:
   (a) initiating a period for starting up said unit by feeding vent gas from the carbonylation unit to the absorber tower, the vent gas including methyl iodide;
   (b) during said period for starting up said unit, supplying a first scrubber solvent to the absorber tower, the first scrubber solvent consisting essentially of chilled acetic acid;
   (c) during said period for starting up said unit, contacting the vent gas with the first scrubber solvent thereby removing methyl iodide from the gas and absorbing methyl iodide and into the first scrubber solvent;
   (d) during said period for starting up said unit, feeding an absorber return stream including first scrubber solvent and absorbed methyl iodide to the light ends column and/or dehydration column;
   (e) during a changeover period, transitioning from start up to steady operation by terminating the supply of first scrubber solvent to the absorber tower ; and
   initiating supply of a second scrubber solvent to the absorber tower, the second scrubber solvent consisting essentially of chilled methanol, so that during at least a portion of said changeover period, acetic acid, methanol and methyl iodide are present in the absorber return stream from the absorber tower;
   (f) thereafter passing at least a portion of said absorber return stream comprising acetic acid, methanol and methyl iodide to the reactor;
   (g) during a steady operation period after said changeover period, contacting the vent gas with the second scrubber solvent thereby removing methyl iodide from the gas and absorbing methyl iodide into the second scrubber solvent;
   (h) during said steady operation period, mixing the second scrubber solvent and absorbed methyl iodide with methanol or a reactive derivative thereof; and
   feeding said absorber return stream including second scrubber solvent and absorbed methyl iodide mixed with methanol or a reactive derivative thereof to the reactor.

13. The method according to claim 12, wherein the vent gas includes methyl acetate and the first and second scrubber solvents are effective to absorb methyl acetate from the vent gas.

14. A method of operating an absorber tower in a carbonylation unit for making acetic acid of the class including a reactor and a light ends column comprising:
   (a) feeding vent gas from the carbonylation unit to the absorber tower, the vent gas including methyl iodide and optionally additional volatile components;
   (b) supplying a first scrubber solvent to the absorber tower, the first scrubber solvent consisting essentially of acetic acid;
   (c) contacting the vent gas with the first scrubber solvent thereby removing methyl iodide and optionally additional volatile components from the gas and absorbing methyl iodide and optionally additional volatile components into the first scrubber solvent;
   (d) feeding an absorber return stream including first scrubber solvent and absorbed methyl iodide and optionally additional absorbed volatile components to the light ends column and/or dehydration column;
   (e) terminating the supply of first scrubber solvent to the absorber tower;
   (f) after the supply of first scrubber solvent to the absorber tower has been initiated, supplying a second scrubber solvent to the absorber tower, the second scrubber solvent comprising methanol, methyl acetate or mixtures thereof;
   (g) contacting the vent gas with the second scrubber solvent thereby removing methyl iodide and optionally additional volatile components from the gas and absorbing methyl iodide and optionally additional volatile components into the second scrubber solvent; and
   (h) after the supply of first scrubber solvent to the absorber tower has been terminated, feeding an absorber return stream including second scrubber solvent and absorbed methyl iodide and optionally additional absorbed volatile components to the reactor.

15. The method according to claim 14, wherein said second scrubber solvent consists essentially of methanol.

16. The method according to claim 14, further comprising the step of chilling the first scrubber solvent prior to supplying it to the absorber tower.

17. The method according to claim 14, further comprising the step of chilling the second scrubber solvent prior to supplying it to the absorber tower.

18. The method according to claim 14, further comprising mixing the second scrubber solvent and absorbed methyl iodide and optional additional absorbed volatile components with methanol or a reactive derivative thereof prior to feeding the used solvent to a carbonylation reactor.

19. The method according to claim 14, wherein the vent gas includes methyl acetate and the first and second scrubber solvents are effective to absorb methyl acetate from the vent gas.

20. The method according to claim 14 wherein termination of supply of first scrubber solvent to the absorber tower and initiation of supply of second scrubber solvent occur substantially simultaneously.

21. The method according to claim 20 wherein termination of supply of first scrubber solvent to the absorber tower and initiation of supply of second scrubber solvent occur within a span of about 5 minutes.

22. The method according to claim 20 wherein termination of supply of first scrubber solvent to the absorber tower and initiation of supply of second scrubber solvent occur within a span of about 20 minutes.

23. The method according to claim 22 wherein the second scrubber solvent consists essentially of chilled methanol and, during the period between termination of supply of first scrubber solvent to the absorber tower and initiation of supply of second scrubber solvent, acetic acid, methanol and methyl iodide are present in the absorber return stream from the absorber tower.

24. The method according to claim 23 wherein at least a portion of said absorber return stream comprising acetic acid, methanol and methyl iodide is passed to the reactor.

25. The method according to claim 23 wherein at least a portion of said absorber return stream comprising acetic acid, methanol and methyl iodide is passed to a location other than a methanol feed system or the light ends column.

26. The method according to claim 23 wherein at least a portion of said absorber return stream comprising acetic acid, methanol and methyl iodide is passed to a catalyst reservoir.

27. The method according to claim 26 wherein at least a portion of said absorber return stream comprising acetic acid, methanol and methyl iodide passed to a catalyst reservoir is thereafter blended with methanol and passed to a carbonylation reactor.

* * * * *